United States Patent
Burkhardt et al.

(10) Patent No.: US 7,375,325 B2
(45) Date of Patent: May 20, 2008

(54) METHOD FOR PREPARING A SAMPLE FOR ELECTRON MICROSCOPIC EXAMINATIONS, AND SAMPLE SUPPORTS AND TRANSPORT HOLDERS USED THEREFOR

(75) Inventors: Claus Burkhardt, Tuebingen (DE); Wilfried Nisch, Tuebingen (DE)

(73) Assignee: Carl Zeiss NTS GmbH, Oberkochen (DE)

( * ) Notice: Subject to any disclaimer, the term of this patent is extended or adjusted under 35 U.S.C. 154(b) by 0 days.

(21) Appl. No.: 11/377,495

(22) Filed: Mar. 16, 2006

(65) Prior Publication Data

US 2006/0261270 A1    Nov. 23, 2006

Related U.S. Application Data

(63) Continuation of application No. PCT/EP04/10364, filed on Sep. 16, 2004.

(30) Foreign Application Priority Data

Sep. 17, 2003    (DE) ................. 103 44 643

(51) Int. Cl.
  *H01J 37/20* (2006.01)
(52) U.S. Cl. ............... 250/307; 250/442.11; 250/306; 250/309; 250/311
(58) Field of Classification Search ........... 250/442.11, 250/306–311
  See application file for complete search history.

(56) References Cited

U.S. PATENT DOCUMENTS

| 5,270,552 | A | | 12/1993 | Ohnishi et al. |
| 5,753,924 | A | * | 5/1998 | Swann ............ 250/443.1 |
| 6,066,265 | A | | 5/2000 | Galvin et al. |
| 6,188,068 | B1 | * | 2/2001 | Shaapur et al. ......... 250/307 |
| 6,194,720 | B1 | | 2/2001 | Li et al. |
| 6,538,254 | B1 | | 3/2003 | Tomimatsu et al. |
| 6,828,566 | B2 | * | 12/2004 | Tomimatsu et al. .... 250/442.11 |
| 6,982,429 | B2 | * | 1/2006 | Robinson et al. ....... 250/492.3 |

(Continued)

FOREIGN PATENT DOCUMENTS

DE    42 26 694 A1    2/1993

(Continued)

OTHER PUBLICATIONS

M.H.F. Overwijk et al.; "Novel scheme for the preparation of transmission electron microscopy specimens with a focused ion beam"; 1993; pp. 2021-2024.

(Continued)

*Primary Examiner*—Jack I. Berman
*Assistant Examiner*—Michael J Logie
(74) *Attorney, Agent, or Firm*—Harness, Dickey & Pierce, P.L.C.

(57) ABSTRACT

In a method for preparing a sample for electron microscopic examinations, in particular with a transmission electron microscope (TEM),
  a) a substrate containing the sample to be prepared on a sample locus is provided in a vacuum chamber,
  b) a protective layer is applied onto a surface of the sample locus,
  c) the sample located under the protective layer is separated from the substrate by an ion beam, the protective layer acting as a mask, and
  d) in the vacuum chamber, the separated sample is removed from the substrate.

35 Claims, 9 Drawing Sheets

U.S. PATENT DOCUMENTS

| | | |
|---|---|---|
| 2002/0022429 A1* | 2/2002 | Yaniv et al. .................. 455/24 |
| 2002/0121614 A1 | 9/2002 | Moore |
| 2002/0166976 A1 | 11/2002 | Sugaya et al. |
| 2003/0089852 A1 | 5/2003 | Ochiai et al. |
| 2003/0089860 A1 | 5/2003 | Asjes |
| 2003/0130114 A1* | 7/2003 | Hampden-Smith et al. . 502/180 |
| 2004/0170843 A1* | 9/2004 | Moritani et al. ............ 428/429 |
| 2005/0035302 A1* | 2/2005 | Morrison .............. 250/442.11 |
| 2006/0011868 A1* | 1/2006 | Kidron et al. ......... 250/492.22 |

FOREIGN PATENT DOCUMENTS

| | | |
|---|---|---|
| DE | 199 46 525 A1 | 5/2001 |
| EP | 1 443 541 A2 | 8/2004 |
| JP | 2003-7241 | 1/2003 |
| JP | 2003-65905 A | 3/2003 |
| WO | 02/095378 A1 | 11/2002 |

OTHER PUBLICATIONS

Shinji Matsui and Katsumi Mori; "New selective deposition technology by electron beam induced surface reaction"; 1986; pp. 299-304.

* cited by examiner

METHOD FOR PREPARING A SAMPLE FOR ELECTRON MICROSCOPIC EXAMINATIONS, AND SAMPLE SUPPORTS AND TRANSPORT HOLDERS USED THEREFOR

CROSSREFERENCES TO RELATED APPLICATION

This is a continuation application of International Patent Application PCT/EP2004/010364, filed Sep. 16, 2004, designating the United States and published in German as WO2005/033650 A2, which claims priority to German application number 103 44 643.5 filed Sep. 17, 2003.

FIELD OF THE INVENTION

The present invention relates to a method for preparing a sample for electron microscopic examinations, in particular with a transmission electron microscope (TEM), and to sample supports and transport holders used therefor.

BACKGROUND OF THE INVENTION

With progressive miniaturization in micro- and nanotechnology, and especially in semiconductor technology, transmission electron microscopy (TEM) of internal interfaces on ion-thinned cross sections is becoming more and more important. Targeted preparation of a selected object position or site, i.e. a specimen or sample lying on or in a sample position or locus of the substrate, is necessary for this. In future MOS components, for example, samples with the gate lengths of from 10 nm to 100 nm and gate oxide thicknesses of a few atomic layers will need to be prepared in a targeted way for high-resolution TEM.

In many areas of materials science, target preparation is also increasingly required on particular micro-regions, for example phase transitions, structure defects, heat influx zones, crack edges, interfaces etc. There are likewise not yet any suitable methods for the targeted preparation of samples for subsequent TEM in the area of the interface between materials and biological tissue, as occur for example in implants.

In order to prepare samples for such electron microscopic examinations, in particular for examinations with a transmission electron microscope (TEM), it is necessary to separate them from their substrate and mechanically fix them.

To this end, it is known from the prior art to separate the sample from the substrate with the aid of a high-energy focused ion beam (FIB) by physical etching or chemically assisted etching. The sample is subsequently taken from the substrate with the aid of a probe, either under a light microscope or still in the FIB device, and then fastened with the aid of this probe on a sample support; see for example U.S. Pat. No. 6,538,254 B1.

US 2003/0089860 A1 describes for example a method in which the sample is separated by FIB from a semiconductor substrate, the position where the sample is to be taken being imaged with the aid of a scanning electron microscope (SEM). The separated sample is removed with the aid of an electrostatically acting manipulator.

US 2002/0121614 A1 describes a method in which the sample is first fully separated from the substrate in the FIB device, before it is fixed on the probe. The probe may in this case be joined to the sample by ion beam induced deposition (IBID) or electron beam induced deposition (EBID) of material from a so-called precursor, by adhesives or electrostatically. The sample is then, for example, transferred onto a sample support and fastened there by material deposition.

WO 02/095378 also describes a method in which the sample is both imaged and separated from the substrate with the aid of FIB. Before separation, a probe is fastened on the sample position by IBID. With the aid of a micromanipulator, the probe with the separated sample is then removed from the substrate and the sample is placed on a TEM support grid and fixed there by IBID. The probe is subsequently separated from the sample with the aid of the ion beam.

DE 42 26 694 discloses a comparable method, in which the sample position is imaged via secondary electron emission in a scanning ion microscope (SIM). The separated sample is fastened on the probe by IBID and can then be observed under an SEM and further processed with an attenuated ion beam, in order to thin the sample for the TEM. The probe comprises a small thin probe head section on which the sample is fastened, and a thick holding section where it is fastened on a micromanipulator. The tip has a diameter of less than 10 µm and the holding section designed as a plate has a thickness of more than 50 µm.

Overwijk et al., "Novel scheme for the preparation of transmission electron microscopy specimens with a focused ion beam", J. Vac. Sci. Technol. B 11(6), 1993, pages 2021-2024 disclose a method in which the sample is likewise imaged and prepared in an FIB device. In order to protect the surface of the sample when the sample is being separated by FIB, the sample is provided by IBID with a tungsten layer which also serves as a mask during the separation. After separation of the sample from the substrate, the substrate with the sample, which is contained in a recess produced by FIB in the substrate, is taken from the vacuum chamber and placed under a light microscope. There, the separated sample is then held via adhesion by a needle and placed on a TEM support by careful manipulation.

All the methods described so far, however, have the disadvantage that the sample is damaged (amorphization) or contaminated (ion implantation) by the high ion energy which is conventionally more than 30 keV. It is then only limitedly suitable for an examination by means of TEM.

Moreover, the damage takes place not only when separating the sample from the substrate by means of FIB but already when looking for the sample position, i.e. when imaging the substrate section containing the sample position in the scanning ion microscope. Although the sample damage is reduced with lower ion energies, the resolution of the imaging is nevertheless greatly reduced with a low ion energy, so that targeted finding of an intended sample position is no longer possible.

Mechanical handling of the prepared sample represents a further problem. This is because after preparation, the minute extremely fragile samples have to be manipulated onto a TEM support grid, which often leads to loss of the elaborately prepared and expensive samples. Often, there is also a poor thermal and electrical contact between the sample and the support grid, which leads to imaging artifacts by charging and heating of the sample.

It is also generally known from the article by Matsui and Mori: "New selective deposition technology by electron beam induced surface reaction" in J. Vac. Sci. Technol B4(1), 1986, pages 299-304, to deposit a tungsten layer on a substrate within a vacuum chamber with the aid of an electron beam (EBID), to which end a precursor, here for example WF6, is introduced into the vacuum chamber via a gas nozzle.

The invention therefore relates to a method for preparing a sample for electron microscopic examinations, in particular with a transmission electron microscope (TEM), having the steps:

a) a substrate containing the sample to be prepared on a sample locus is provided in a vacuum chamber, b) a protective layer is applied onto a surface of the sample locus, c) the sample located under the protective layer is separated from the substrate by an ion beam, the protective layer acting as a mask, and d) within the vacuum chamber, the separated sample is removed from the substrate.

Such a method is known from U.S. Pat. No. 6,188,068 D1. In the known method, the sample is cut free by FIB and then joined either to a TEM sample support and removed from the substrate using it, or taken using a probe on which the sample is held in a suitable way. The sample is then placed on a TEM sample holder.

The inventors of the present application have recognized that precisely the combination of a protective layer and handling still in the vacuum chamber avoids many problems which are prevalent in the prior art. The protective layer significantly reduces the risk of damage to the sample during separation from the substrate, while handling still in the vacuum chamber avoids mechanical damage. In the vacuum chamber, it is now possible to take the separated sample with great reliability and reproducibility, for example by adhesion. The loss of sample during handling, often to be observed in the prior art, is thus avoided.

Although Overwijk et al. also describe manipulation of the sample by using adhesion on a needle tip, this is nevertheless carried out under a light microscope, i.e. not in a vacuum. The inventors of the present application have now recognized that adhesion can be controlled better in a vacuum and is more reproducible than under atmospheric conditions. According to the inventors' understanding, this is attributable to the varying humidity under atmospheric conditions. In fact, the sample will adhere better or worse on the needle depending on the degree of humidity. In a vacuum, the moisture film required for the adhesion can now be provided in a controlled way without dependence on external influences.

Another advantage with this method is that the protective layer can be used as a mask so that, instead of focused i.e. high-energy ion beams, it is possible to use low-energy ion beams in the manner of an ion shower for the separation, which have a smaller position resolution than the high-energy ions in FIB. The position resolution required for separating the sample is achieved here by the protective layer mask, which has an even higher position resolution than FIB. This electron beam deposition of the protective layer also already avoids many of the aforementioned disadvantages. This is because when the protective layer is being deposited, the surface of the sample is not damaged by the electrons which can be used according to the invention, as is caused by the high-energy ion beams used for this in the prior art.

SUMMARY OF THE INVENTION

In view of the above, it is one object of the present invention to improve the aforementioned method so that reliable and straightforward manipulation of the sample is possible.

According to the invention, this and other objects are achieved in the known method in that the sample is joined in step c) or d) to a TEM sample support which is moved by a manipulator and comprises, as the holding end, a TEM support grid, a metal angle segment disk or a copper half-disk and, fastened thereto or formed integrally therewith, a needle on which a thin tip is formed, the sample support being used for preparation and simultaneous mechanical fixing of the sample.

The object underlying the invention is fully achieved in this way.

In fact, the inventors of the present invention have recognized that good manipulation of the sample, on the one hand, and reliable fastening of the sample on the TEM sample support, on the other hand, are possible by using a TEM sample support designed in this way. Because a sample support which remains on the sample is used, the risk of damage to the prepared sample during the subsequent manipulation is reduced significantly. Complicated and risky removal of the sample from the probe and its subsequent fastening on the sample support are obviated.

Preferably, the sample support is gripped at its thicker holding end by the manipulator and fastened with its thin tip to the sample in step c) or d), more preferably the sample support, preferably its thin tip, being fastened to the sample by electron beam deposition or using a drop of adhesive in step c) or d).

The sample support therefore represents, so to speak, the connection between the nano world on its tip and the micro world at its holding end, where it can be gripped and moved by a conventional micromanipulator.

The geometry of the sample support used for this has the advantage that it represents a connection between the nano and micro worlds which is easy to produce in design terms.

The holding end is preferably designed as a circle segment or sector, i.e. as an angle segment disk or grid, in which case the aperture angle may lie between 30° and 180°, and is preferably 90°. According to a preferred exemplary embodiment, the holding end is designed as a quadrant of a circle.

This design has the advantage that viewing is not perturbed either for the ion beam or for the electron beam, since only a small surface is covered by the holding end.

In view of the above, it is a further object of the present invention to provide a TEM sample support having as the holding end for a manipulator a TEM support grid, preferably designed as a circle segment or sector, or a metal angle segment disk and, fastened on the TEM support grid or the angle segment disk or formed integrally therewith, a needle which can be fastened with its thin tip on a sample for electron microscopic examinations, in particular with a transmission electron microscope (TEM), preferably the TEM support grid or the angle segment disk having a radius of from approximately 500 µm to approximately 2 mm and the needle having a length in the region of the radius of the TEM support grid, the needle having a diameter of from approximately 100 nm to approximately 10 µm in the region of its thin tip.

U.S. Pat. No. 6,066,265 describes a method with which also the novel TEM sample support can also be produced in principle. To this end, a three-layered wafer is prepared with a thicker lower silicon layer and a thinner upper silicon layer, a layer of silicon oxide being arranged as an etch stop layer between the two silicon layers. An etching mask is applied onto both silicon layers. The upper etching mask corresponds to the plan view of the support grid plus needle from above, and the lower etching mask corresponds only to the plan view of the support grid from below.

Then, the silicon around the etching mask is first etched away. This creates the holding end, whose thickness is determined by all three layers, and the needle joined integrally with it, whose thickness is determined by the upper, thinner silicon layer and initially also the layer of silicon oxide. The silicon oxide is then removed from the lower side of the needle in a further working step.

In general, it is preferable for the protective layer to be deposited on the surface in step b) with the aid of a preferably focused particle beam, in particular a focused electron beam (EBID), ion beam or photon beam.

Besides EBID, the protective layer may also be deposited with an ion beam or a photon beam, the energies respectively being selected so as to avoid or greatly minimize damage to the sample.

According to a further object, the protective layer is applied onto the surface as a mechanical cover in step b), a nanotube or fine nanowire preferably being applied onto the surface as the mechanical cover.

This is an alternative to the protective layer deposited via a particle beam. The mechanical cover fulfills the same purpose and, like the electron beam, has the advantage that the sample is not damaged. Like the deposited protective layer, the dimensions of the mechanical protective layer lie in the nm range.

According to still another object, the protective layer is applied onto the surface by spraying or evaporation, preferably sprayed onto the surface with the aid of a shadow mask.

This is another alternative to a protective layer deposited via a particle beam. The sprayed or evaporated protective layer fulfills the same purpose and, like the electron beam, has the advantage that the sample is not damaged.

According to another object, in step b) the protective layer to be applied onto the surface is of a material that is only weakly etchable by ions.

The advantage here is that the protective layer provides sufficient protection for the covered sample during the subsequent separation of the sample from the substrate, which is done by means of an ion beam. Tungsten in particular, which is already tried and tested as a protective layer material in another context, but also platinum, carbon compounds or in general metallorganic compounds are suitable as a material for the cover.

It is further preferable that in step a), the substrate is placed in a scanning electron microscope (SEM) and a section of the substrate containing the sample position is imaged using the SEM.

This provides particular advantages because the sample is also imaged by SEM and not by FIB, so that damage does not already take place during localization of the sample to be prepared.

It is still another object, that the sample is separated from the substrate by a broad ion beam (selected area ion beam: SAIB) in step c), a low-energy ion beam preferably being used whose ion energy is less than 10 keV, preferably less than 5 keV. This measure per se is also novel and inventive in the known method.

Here, it is advantageous that the risk of damage to the sample is reduced since the broad and low-energy ion beam cannot seriously damage the sample through the protective layer. Damage by ions arriving laterally on the sample, i.e. circumventing the protective layer, is also only of minor importance since radiation damage is minimized by the low-energy ions.

It is preferable that in step c), the sample is first partially separated from the substrate, then the sample support is joined to the sample, and then the sample is fully separated from the substrate, the full separation being carried out by the ion beam or by breaking the sample out in a mechanical way.

Here, it is advantageous that the sample support is fastened to the sample at a time when the sample is still mechanically fixed via the substrate. This avoids damage to the sample by tipping or tilting when the sample support is being fastened. The sample support can furthermore be fastened at an accurately establishable location on the sample; this is because the sample cannot "slip" when fastening since it is still fixed.

In the novel method, it is then preferred that the sample removed from the substrate is placed with the sample support in a TEM sample rod, on which the sample support is subsequently fastened.

Here, it is advantageous that manipulation no longer has to be carried out on the sample itself after fastening it to the TEM sample support, the further transport and fastening measures being carried out using the TEM sample support.

According to another object of the invention, in the known method in step c) or d), the sample is held by adhesion on a hydrophilic surface of a transport holder moved by a manipulator.

Here, it is advantageous that the sample does not have to be exposed to the stresses which are involved in fastening on the sample support. Furthermore, the sample is fully available for the subsequent examination after removal and placement, no regions being covered by a sample carrier "soldered on". The complicated and risky removal of the sample support from the sample is obviated in particular when, for geometrical reasons, the sample can only be gripped for removal from the substrate at the regions which must again be free for the subsequent examination. It is now furthermore possible to deposit a plurality of samples successively on a support before it is taken from the SEM for further processing.

It is then preferable that that in step c) or d), a moist gas is directed onto the hydrophilic surface before removal of the sample from the substrate.

Here, it is advantageous that the moist gas forms a moisture film which ensures reliable holding of the sample on the hydrophilic surface. The moisture film can be generated reproducibly since the novel method is carried out in a vacuum chamber, which is not the case in the prior art according to Overwijk et al. when the sample is manipulated in a light microscope under atmospheric conditions.

It is then furthermore preferred that in step d), a dry gas is directed onto the hydrophilic surface after removal of the sample from the substrate.

In this methodologically simple way, it is possible to ensure reliable detachment of the sample from the hydrophilic surface. The sample can thus be positioned in a defined way. This is not possible in the prior art because the hydrophilic surface, which has dimensions in the nanometer range or lower micrometer range, cannot thereby be dried reproducibly under atmospheric conditions.

It is then furthermore preferred that the hydrophilic surface has a slot, the sample being positioned on the hydrophilic surface so that it comes to lie over the slot, and that after removal from the substrate the sample is placed on a base engaging into the slot, and that the hydrophilic surface is then removed from the sample in the direction of the base.

Here, it is advantageous that the sample can be transferred onto the base in a defined way, but without incurring the risk of mechanical damage.

On the other hand, it is also possible to place the sample on a sample holder with a fork structure, the prongs of the fork so to speak gripping on both sides next to the hydrophilic surface below the sample.

A drawn glass capillary or a patch pipette, on the tip of which the hydrophilic surface is formed, may be used as the transport holder.

According to still another object of the invention, a drawn glass capillary is provided, for example in the manner of a patch pipette, having a hollow tube open at its tip and a hydrophilic surface fastened on the tip, as a transport holder for holding a sample for electron microscopic examinations, in particular with a transmission electron microscope (TEM).

This feature offers a design advantage since, in the simplest case, it is possible to use an existing patch pipette such as that used in the patch-clamp technique. It merely needs to be provided with a hydrophilic surface protruding beyond its tip. The moist gas, and subsequently the dry gas, can then be directed onto the hydrophilic surface through the patch pipette.

In the novel method, it is alternatively preferable for the sample to be pressed in step d) by a hydrophobic surface of the transport holder against the hydrophilic surface.

In a simply designed way, this measure further increases the reliability when transporting the sample since it is held not only by adhesion but also by a clamping action. Because the second surface is hydrophobic, the fragile sample remains reproducibly on the hydrophilic surface after the pincer formed by the two surfaces is opened, and can be positioned in a defined way.

A gripper having two nano-jaws may be used as the transport holder, one jaw of which comprises the hydrophilic surface and the other jaw of which comprises the hydrophobic surface.

According to another object, the invention provides a gripper having two micromechanical pincer elements on which each a nano-jaw is fastened, one jaw comprising a hydrophilic surface and the other jaw comprising a hydrophobic surface, as a transport holder for gripping a sample for electron microscopic examinations, in particular with a transmission electron microscope (TEM), preferably the nano-jaws having a length of from approximately 100 nm to approximately 10 μm and a width of from approximately 100 nm to approximately 10 μm.

The nano-jaws may be coupled by EBID or IBID to the front ends of pincer elements of a micro-gripper, as produced for example by Nascatec GmbH, Ludwig Erhard Straβe 10, 34131 Kassel and available from NanoAndMore GmbH, Merkstraβe 22, 64283 Darmstadt. On the other hand, it is also possible to reprocess, and thus so to speak sharpen, the front ends of the pincer elements of such micro-grippers by FIB.

With this further miniaturization, it is advantageous that the nano-jaws cause a spring effect at the front end of the micromechanical pincer elements, which further reduces the risk of damage to the fragile sample.

It shall be mentioned that, with the novel method, it is possible to prepare samples which have a thickness of from approximately 5 to approximately 200 nm and a length of from approximately 1 to approximately 200 μm. The height is from approximately 100 nm to approximately 100 μm.

Other advantages and features will be found in the following description and the appended figures.

It is to be understood that the features mentioned above and yet to be explained below may be used not only in the combination respectively indicated, but also in other combinations or separately, without departing from the scope of the present invention.

BRIEF DESCRIPTION OF THE DRAWINGS

Embodiments of the invention are represented in the figures and will be explained in more detail below in the following description.

DESCRIPTION OF PREFERRED EMBODIMENTS

Figure 1:
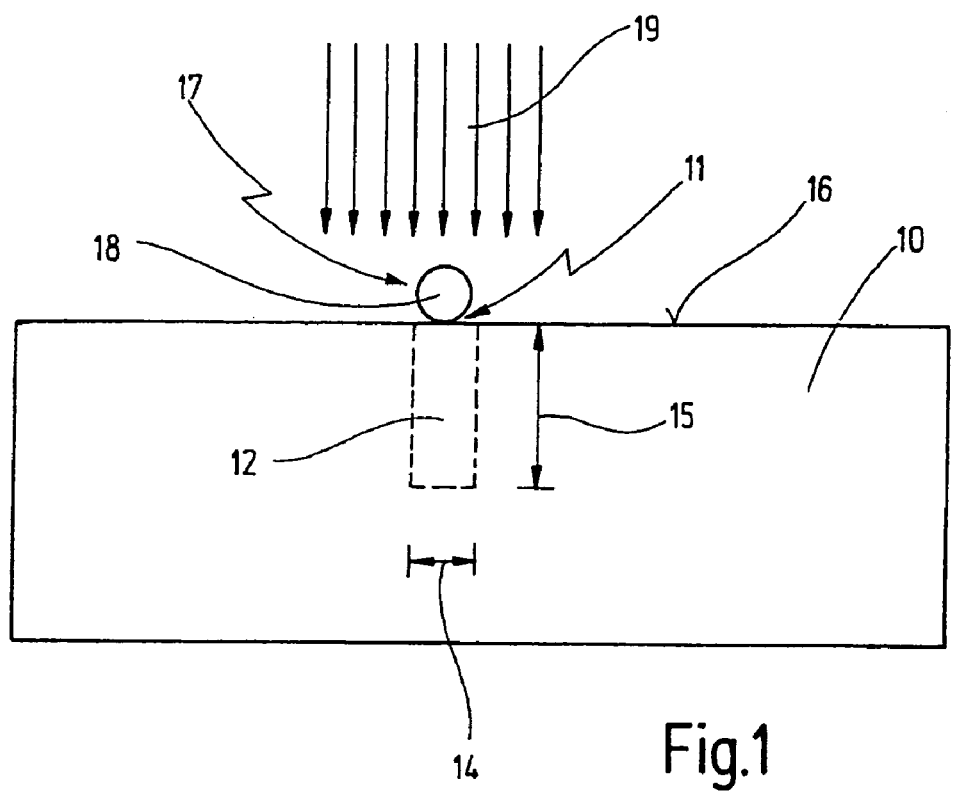
FIG. 1 shows a substrate in a side view with the sample represented in dashes, as well as a nanowire covering the sample locus and an indicated SAIB.

In FIG. 1, 10 denotes a substrate from which a sample 12 represented by dashes in FIG. 1 is to be taken from a sample position or locus 11. The sample 12 is intended to be prepared for examinations with a transmission electron microscope (TEM), to which end it is first necessary to separate it from the substrate 10 and then mechanically fix it.

The sample has a thickness 14 of from 5 to 200 nm and a height 15 of from 100 nm to 100 μm.

On one surface 16 of the substrate 10, and therefore also the sample position 11, a mechanical cover 17 is applied in the form of a nanowire 18 which constitutes a protective layer for the sample 12 to be taken from the sample position 11 under the surface 16.

As will be described in more detail below, the sample 12 can now be separated from the substrate 10 using a broad ion beam indicated by 19. This is because the ion beam 19 now erodes material from the substrate on all sides of the sample 12 protected by the nanowire 18, the sample 12 "remaining" under the protective layer formed in this way.

Figure 2:
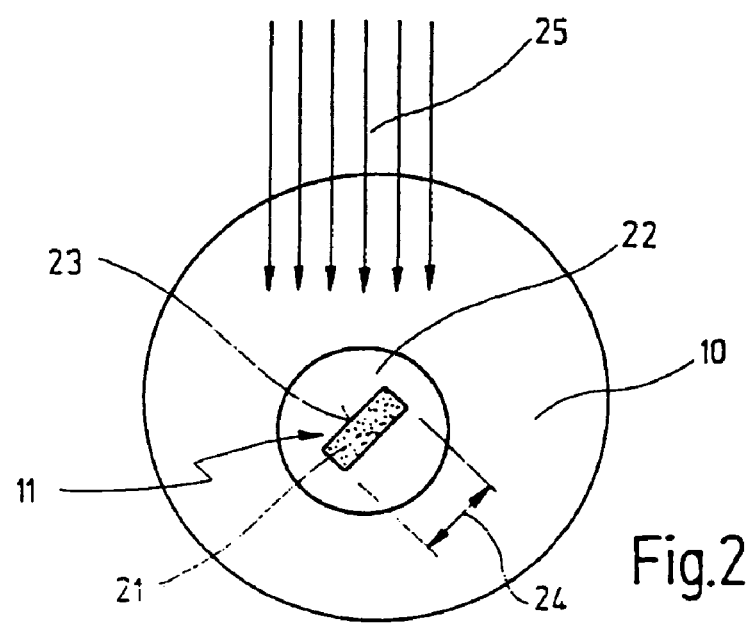
FIG. 2 shows a substrate in a plan view with a shadow mask, which exposes a sample locus.

As an alternative to a mechanical cover 17, as will now be described with reference to FIG. 2, a protective layer 21 may also be sprayed onto the sample position 11. To this end, in the region of the sample position 11 on the substrate 10, a shadow mask 22 is applied which covers the region around the sample position 11 but contains a window 23 whose thickness and length are adapted to the sample 12. The sample is thus provided with a length of from 1 to 200 μm, indicated by 24.

The protective layer 21, which consists of a material, only weakly etchable by ions, is now applied onto the sample position 11 using a spray beam indicated by 25. After the shadow mask 22 is removed, the sample 12 can then be separated from the substrate 10 by a broad ion beam 19, as indicated in FIG. 1.

Figure 3:
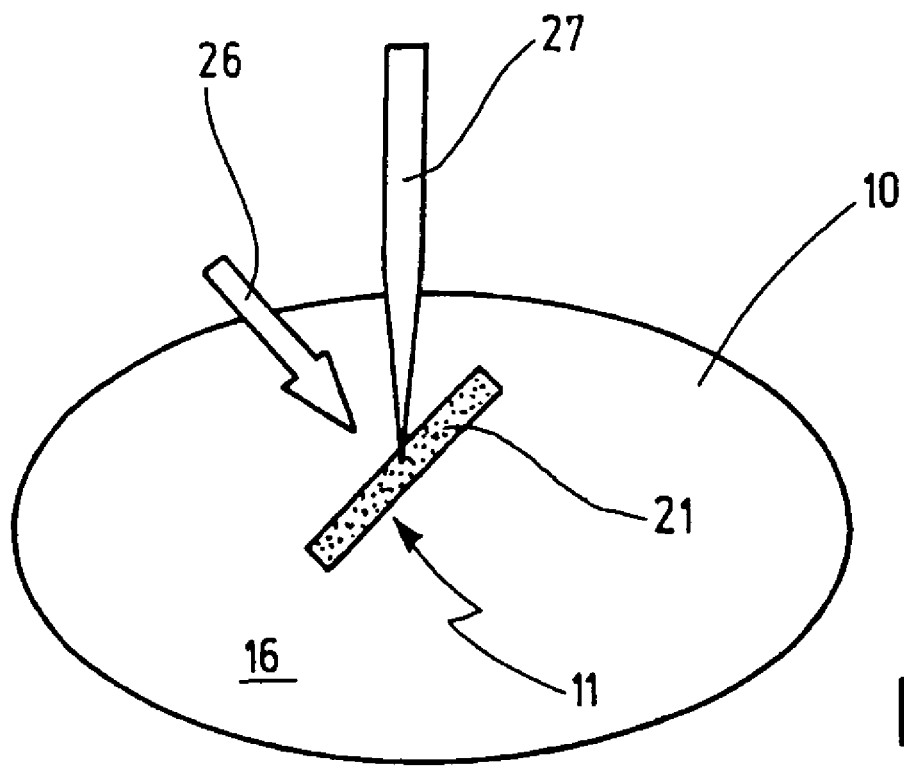
FIG. 3 shows a schematic view of a substrate in which a protective layer is applied onto the surface of the sample locus.

As an alternative to the spraying described in connection with FIG. 2, the protective layer 21 may also be deposited on the surface 16 with the aid of a focused particle beam as schematically represented in FIG. 3.

In order to produce the protective layer 21, material from a so-called precursor is deposited on the surface 16 using a focused electron beam 27. Because the electron beam 27 is finely focused, the sample position 11 can, despite its small dimensions, still be provided precisely with a protective layer 21 of a material weakly etchable by ions. This electron beam induced deposition (EBID) of material is known per se, and is described for example in the article by Matsui and Mori mentioned in the outset. Tungsten in particular, but also platinum, carbon compounds or in general metallorganic compounds are suitable as a material for the protective layer 21.

As an alternative to a focused electron beam 27, the protective layer 21 may also be deposited using an ion beam or using a photon beam, the energies respectively being selected so as to avoid or at least greatly minimize damage to the sample 12.

Figure 4:
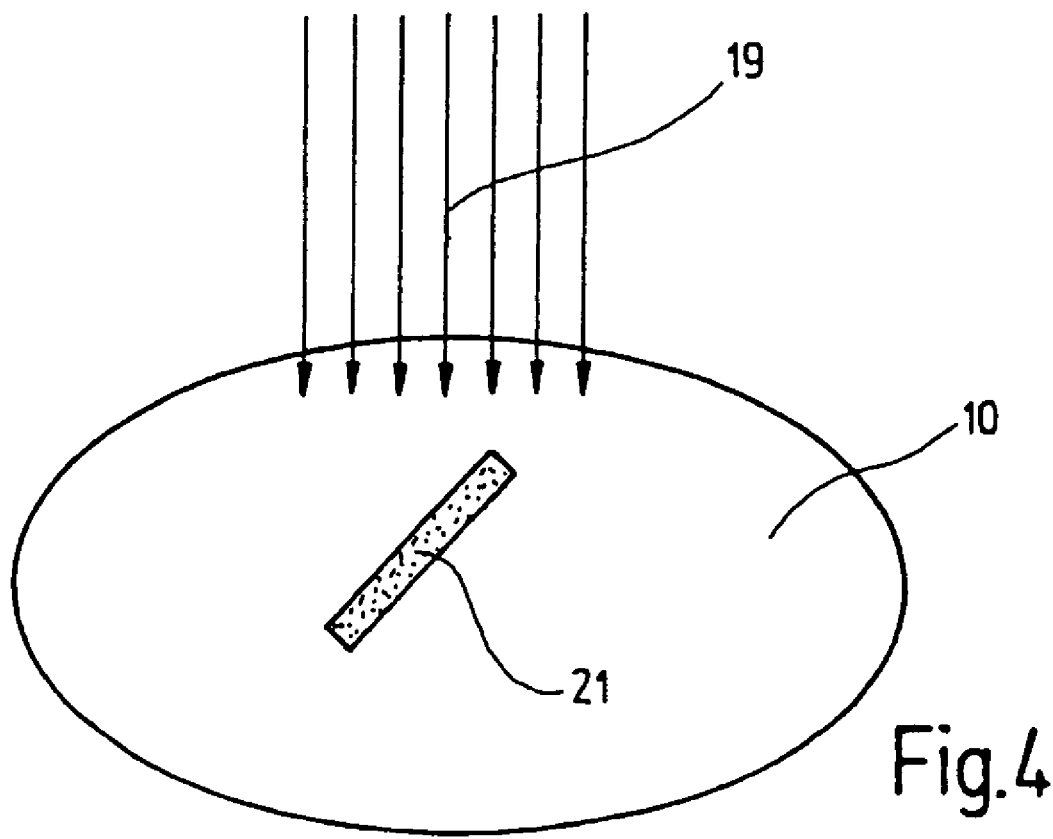
FIG. 4 shows a schematic view of a substrate in which the sample is separated from the substrate by an ion beam.

Since the protective layer 21 consists of a material weakly etchable by ions, during the subsequent separation of the sample 12 from the substrate 10 it provides sufficient protection for the sample covered in this way, which is now separated from the substrate 10 with the aid of the broad ion beam 19 as schematically represented in FIG. 4. The broad ion beam 19, which is also referred to as a selected area ion beam (SAIB), has an ion energy which is preferably less than 5 keV. This further reduces the risk of damage to the sample 12, as the broad and therefore low-energy ion beam cannot damage the sample 12 through the protective layer 21.

Figure 5:
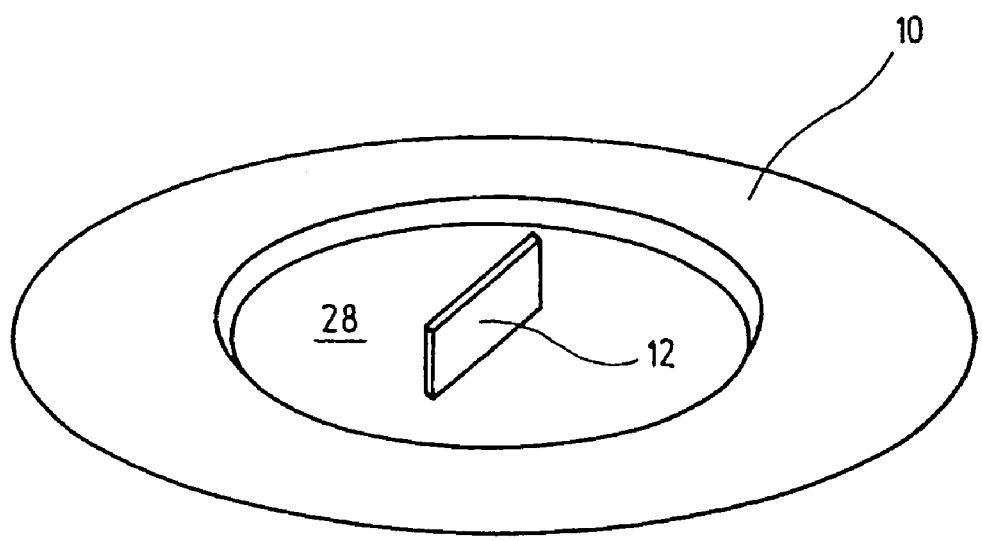
FIG. 5 shows a representation as in FIG. 4, the sample being separated at least circumferentially from the substrate.

A region 28, for example a circular region, of eroded material is created around the sample 12 in the substrate 10, so that the sample 12 lies as a lamella in the region 28 and remains joined to the substrate 10 only on its lower side, as indicated in FIG. 5.

Figure 6:
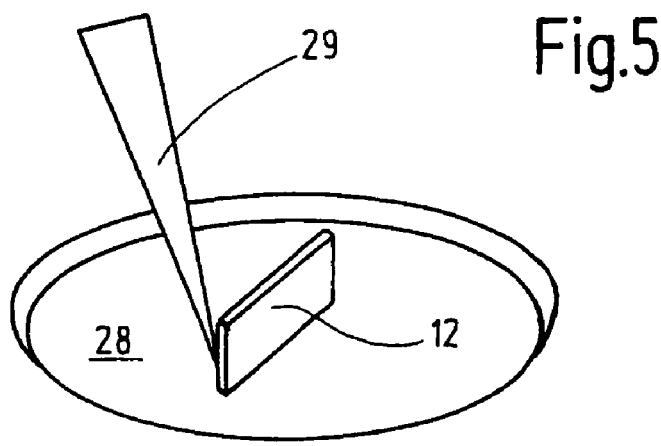
FIG. 6 shows a representation as in FIG. 5, the sample being fastened on the tip of a needle.

The sample 12 is then joined to the tip 29 of a sample support or transport holder, as indicated in FIG. 6. The sample 12 may be joined to the tip 29 by EBID, with the aid of an adhesive or by surface tension, as will be explained in more detail below.

Figure 7:
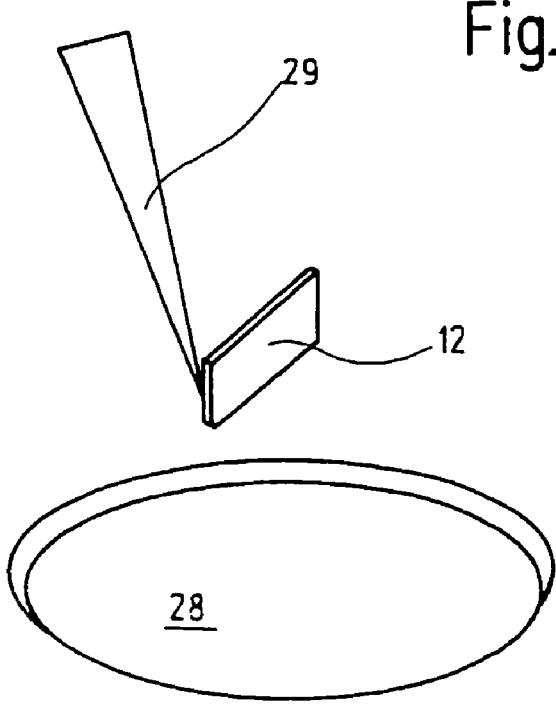
FIG. 7 shows a representation as in FIG. 6, the sample fastened on the needle being raised from the substrate.

The sample 12 is then lifted out of the region 28 with the aid of the tip 29, as indicated in FIG. 7.

Figure 8:
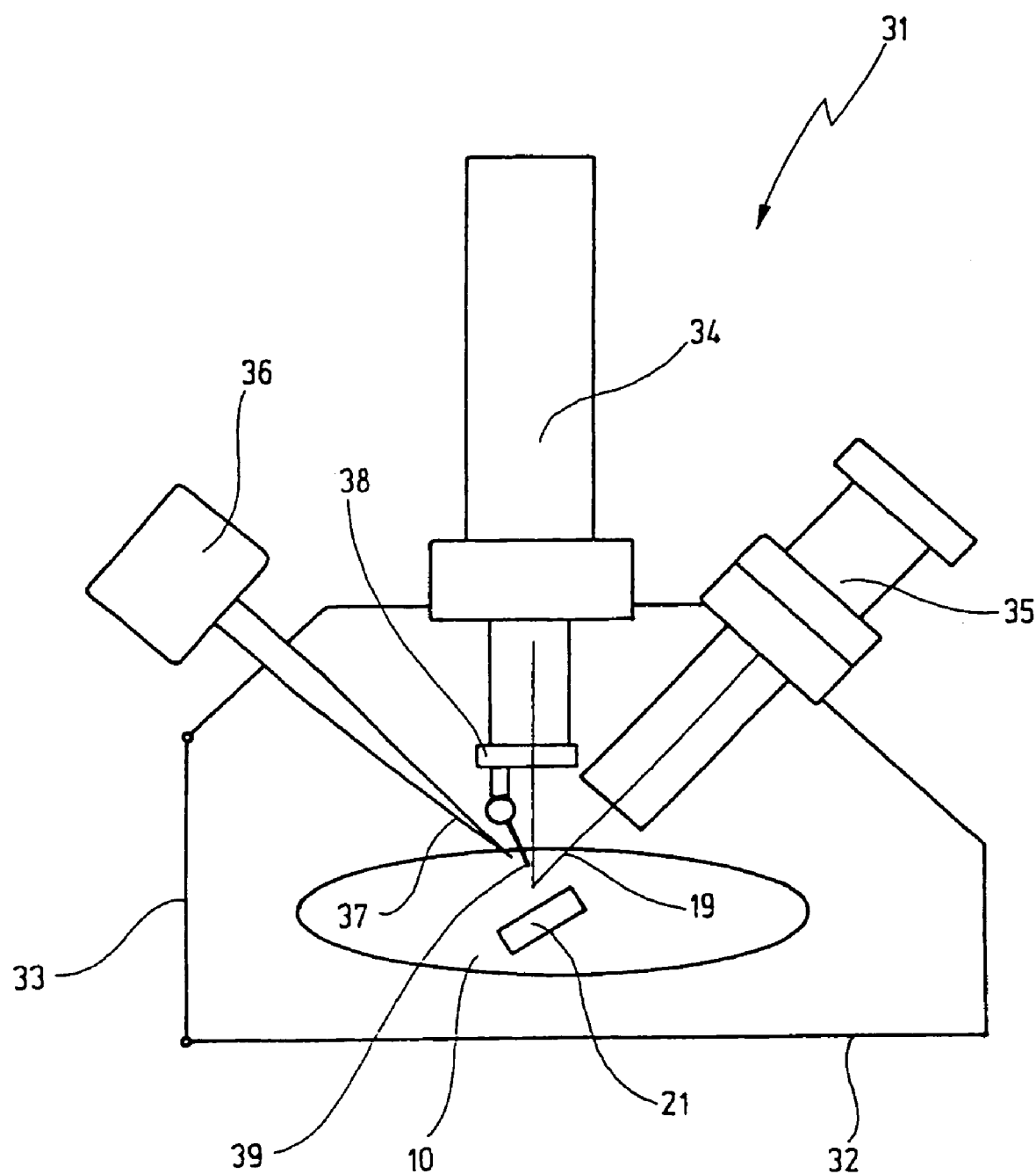
FIG. 8 shows a schematic representation of a scanning electron microscope in which a substrate is arranged, a sample of which is intended to be prepared and analyzed.

The preparation of the sample 12 as described so far in relation to FIGS. 1 to 7 is carried out under a vacuum in a scanning electron microscope (SEM) 31, as illustrated by a schematic side view in FIG. 8.

The SEM comprises a vacuum chamber 32, which is accessible from outside via a door indicated by 33 so that the substrate 10 can be positioned within the vacuum chamber 32.

An electron source 34, with appropriate optics which are used both for imaging the sample position and for depositing the protective layer by means of EBID, protrudes into the vacuum chamber 32. An ion source 35 which generates the broad ion beam 19, by which the sample is separated from the substrate, also protrudes into the vacuum chamber 32. A precursor chamber 36 is furthermore provided, which protrudes with its gas nozzle 37 into the vacuum chamber 32 where it delivers the precursor from which the material for the protective layer, and optionally for joining the sample to the tip of a sample support or transport holder, is deposited.

Lastly, a manipulator 38 is also provided which carries a gripper 39, which can be moved by the manipulator 38 in the region of the substrate 10 so that it can directly engage the sample 12, or may grip a sample support or transport holder which is fastened on the sample.

All the steps for preparing the sample can be carried out in the vacuum chamber 32. The sample to be prepared is first localized with the aid of imaging by the electron beam source 34, which is possible without damaging the sample. The protective layer 21 is then deposited on the substrate 10, which is done with the aid of the electron beam source 34 and the precursor. Here as well, the sample is not damage.

Lastly, the sample is separated from the substrate 10 with the aid of the broad ion beam 19, on the one hand the sample being protected against damage by the protective layer 21, and on the other hand the risk of damage to the sample already being greatly reduced by the broad, i.e. low-energy ion beam 19. Therefore, damage by ions arriving laterally on the sample, i.e. circumventing the protective layer 21, is also only of minor importance.

The sample may be removed fully from the substrate 10 before it is fastened on the tip 29 known from FIG. 6, or may be engaged directly with the aid of the gripper 39. On the other hand, it is also possible to leave the sample still joined to the substrate 10 on its lower side and initially fasten the tip 29 on the sample or grip it with a gripper 39. In a subsequent method step, the sample is then definitively separated from the substrate 10, which may be done either with the aid of the ion beam 19 or by mechanically breaking the sample out.

The sample may thus be fully separated from the substrate 10 in the SEM 31, without risking damage to the sample by high-energy ions. Furthermore, the sample may be mechanically fixed while still in the vacuum chamber 32, for example on a TEM sample support which is then placed in a conventional TEM sample rod and fastened there. In this way, only minor transport distances and fixing and release processes are necessary, so that mechanical damage to the sample is likewise substantially avoided.

Figure 9A:
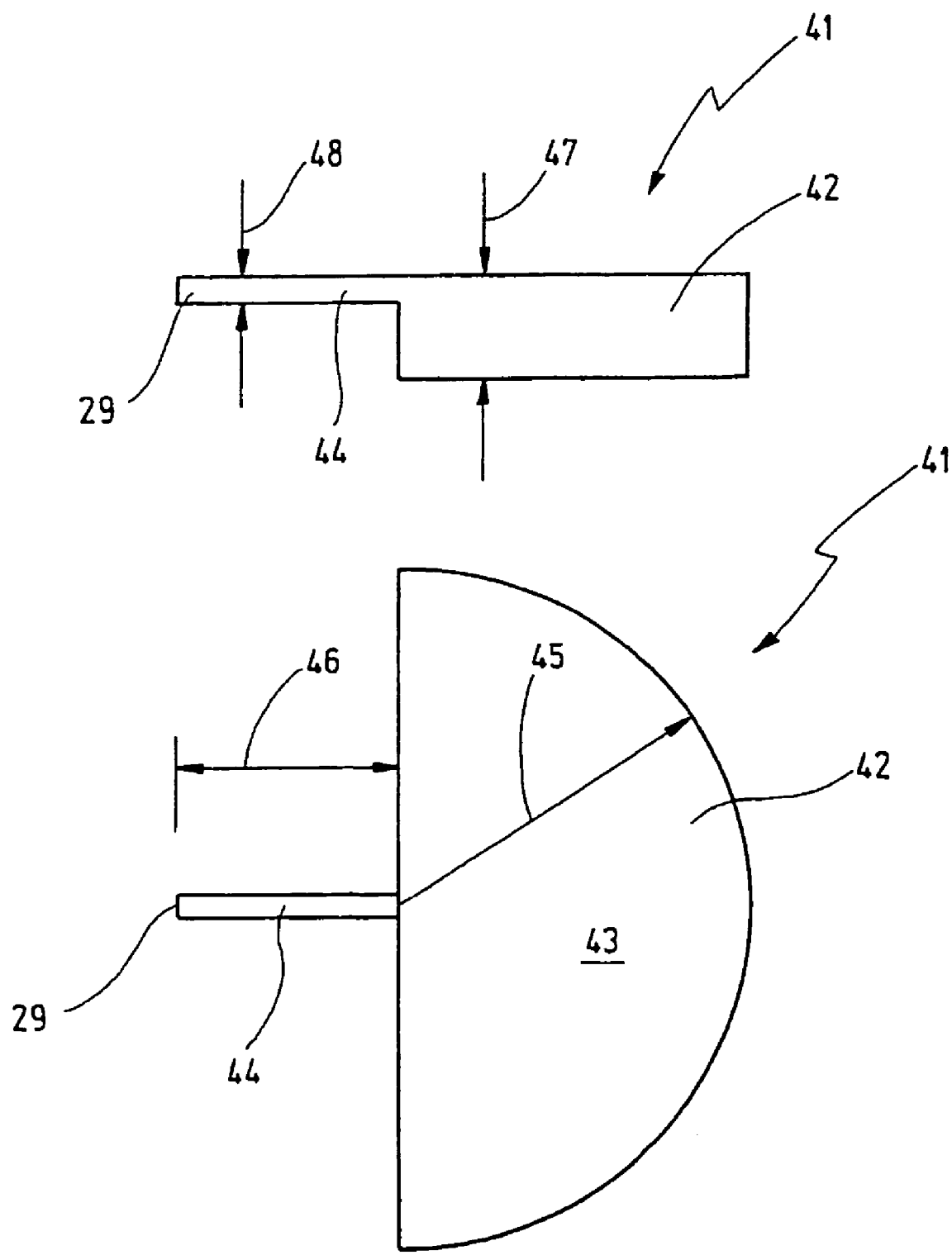
FIG. 9a shows a side view and plan view of a TEM sample support with a TEM support grid and a needle, such as may be used in the method steps of FIGS. 6 and 7.

FIG. 9a shows a TEM sample support 41 at the top in a side view and at the bottom in a plan view, which is used both for preparing and for mechanically fixing the sample. The sample can thus remain on the TEM sample support 41, which significantly reduces the risk of damage to the prepared sample during the subsequent manipulation.

The TEM sample support comprises a thick holding end 42, namely a semicircular TEM support grid 43 on which a needle 44 that converges into the tip 29 known from FIGS. 6 and 7 is integrally formed. The TEM support grid 43 has a radius 45 which lies in the range of from approximately 500 μm to approximately 2 mm. The radius 45 is preferably adapted to the standard diameter of recesses in TEM sample rods, which are 2.3 or 3.0 mm. The needle 45 has a length 46 which lies in the range of the dimensions of the radius 45.

47 indicates a thickness of the TEM support grid 43 which lies in the range of from 10 μm to 650 μm, and which preferably corresponds to a standard wafer thickness of 635 μm.

At its tip, the needle 44 has a diameter 48 which lies in the range of from 100 nm to 10 μm.

Figure 9B:
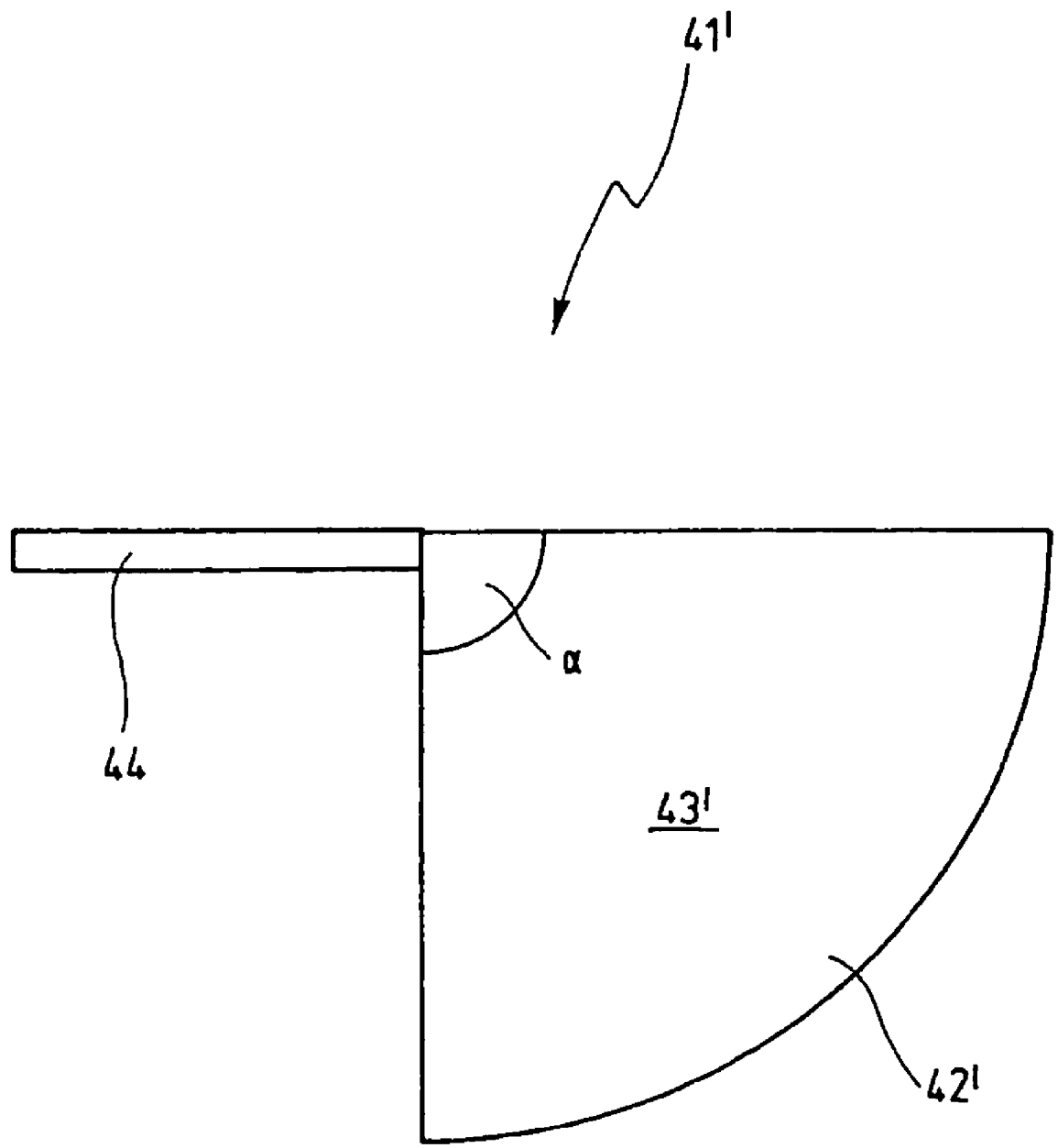
FIG. 9b shows another embodiment of a TEM sample support, such as may be used in the method steps of FIGS. 6 and 7.

FIG. 9b shows another TEM sample support 41', which is equivalent in cross section to the structure of the sample support 41 on FIG. 9a. The difference in structure, however, is the thick holding end 42' which, in contrast to FIG. 9a, is not a semicircular TEM support grid 43 but a circle-quadrant TEM support grid 43'.

The TEM support grid 43 may in general be designed as a circle segment or sector, its aperture angle a indicated in FIG. 9b lying between 30° and 180°, and according to FIG. 9b it is preferably 90°.

Compared with the TEM sample support 41 of FIG. 9a, the TEM sample support 41' of FIG. 9b has the advantage that the area covered by the holding end 42' is smaller, so that it hinders neither the ion beam 19 when cutting the sample free nor the electron beam 25 from the electron source 34 when imaging the sample position.

A method with which the TEM sample support 41 of FIG. 9a or b can be produced in principle is known from U.S. Pat. No. 6,066,265 mentioned at the outset.

Instead of as a TEM support grid 43 or 43', the holding end 42, 42' may also be designed as a metal disk or foil in the form of an angle segment, for example a semicircle or a circle quadrant. For example, it is possible to use a circle-quadrant disk of copper foil with a thickness of approximately 70 μm, onto which a thin tungsten wire with a diameter of 50 μm is bonded as a needle, which converges into a thin tip of for example 10 μm. On the other hand, it is also possible to produce the quadrant disk from tungsten foil such that the needle can be produced integrally with it by microtechnology.

Figure 10:
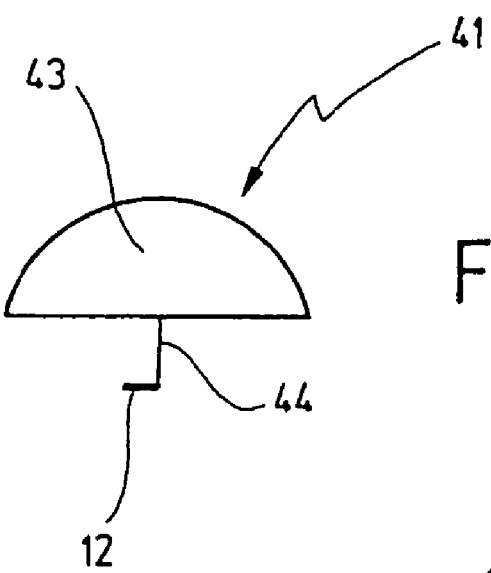
FIG. 10 shows a plan view of the TEM sample support of FIG. 9, with a sample fastened on the tip of the needle.

FIG. 10 shows the TEM sample support 41 of FIG. 9a, the needle 44 now being fastened to a sample 12. This fastening of the sample 12 on the needle 44 may be carried out by EBID or using a drop of adhesive.

Figure 11:
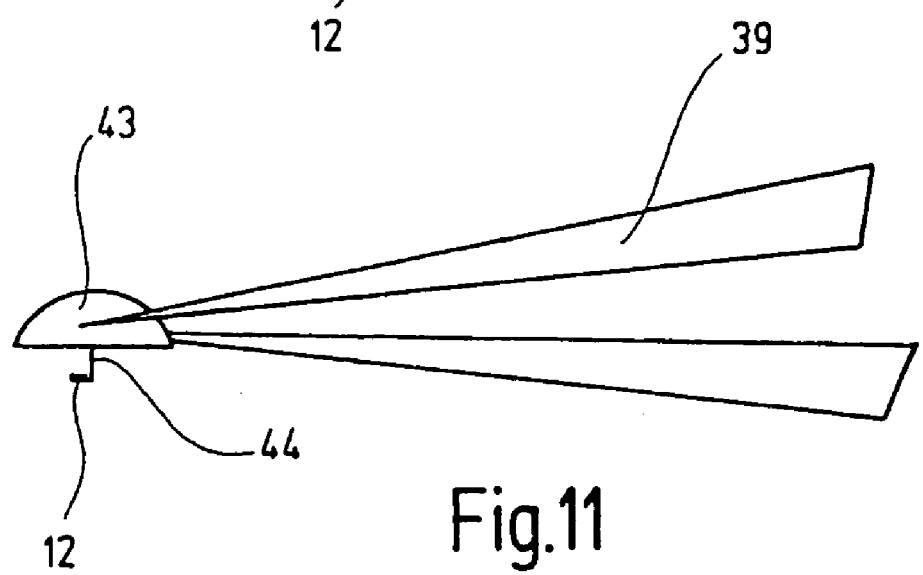
FIG. 11 shows the TEM sample support of FIG. 10, which is engaged on the TEM support grid by pincer elements of a gripper.
Figure 12:
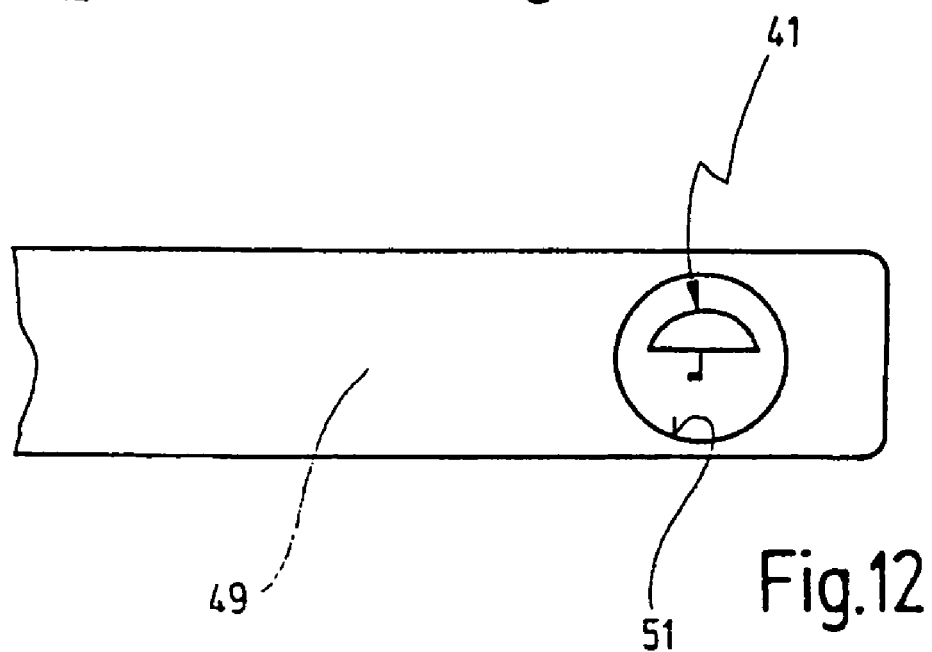
FIG. 12 shows a TEM sample rod into which the TEM sample support of FIG. 10 is placed.

The TEM sample support 41 is now gripped on the TEM support grid 43 by the gripper 39 known from FIG. 8, which is represented in FIG. 11.

The gripper 39 moved by the manipulator 38 of FIG. 8 now places the TEM sample support 41 in a reception space 51 provided in a TEM sample rod 49, where the TEM sample support 41 is mechanically fixed via its TEM support grid. This may be done using a sprung cap or using a threaded ring, as is known per se.

The sequence of FIGS. 7 to 12 represents the transition from the nano world represented by the sample 12 to the micro world, as is embodied by the TEM support grid 43, 43'. The transition to the macro world then takes place via the gripper 39 and the TEM sample rod 49.

The TEM sample support 41, 41' therefore represents the important connecting element between the nano world and the macro world, the sample 12 having to be fastened only once on the needle 44, and all the other steps taking place without further direct manipulation of the sample 12.

Figure 13:
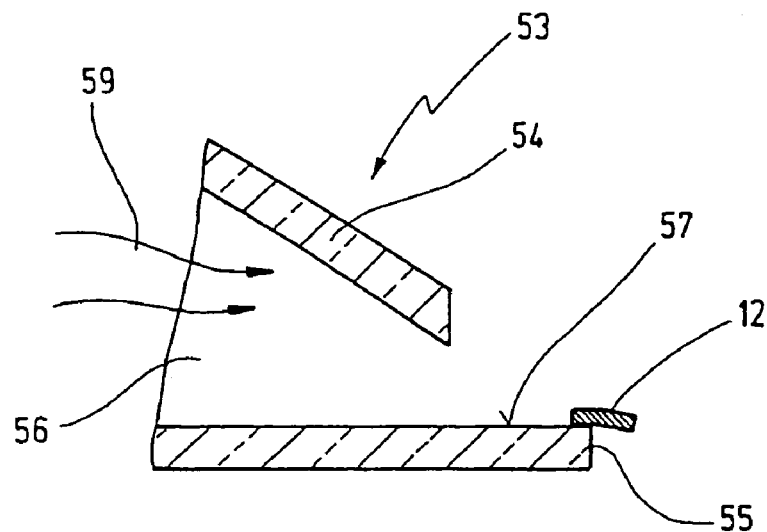
FIG. 13 shows, in a sectional schematic side representation, a drawn glass capillary with a hydrophilic surface on which the sample of FIG. 5 is fastened.

As an alternative to fastening of the sample 12 on a sample support as described so far, the sample 12 may also be gripped by adhesion on a hydrophilic surface of a transport holder 53 moved by the manipulator 38 of FIG. 8. A drawn glass capillary, for example, as is known as a patch pipette 54 from the patch-clamp technique, may be used as the transport holder 53. Such a patch pipette 54 is shown in a greatly enlarged schematic view in the region of its tip 55 in FIGS. 13 and 14. In a manner which is known per se, the patch pipette 54 consists of a tube 56 which is open at its tip 55, a hydrophilic surface 57 being formed or fastened on the tip 55. The hydrophilic surface 57 is part of the patch pipette 54 in the embodiment according to FIG. 13, while the hydrophilic surface 57 in the embodiment according to FIG. 14 is a nano-jaw 58 which is fastened on the patch pipette 54 by EBID or IBID.

The sample 12 adheres to the hydrophilic surface 57 by adhesion, so that it is not exposed to stresses which could occur when fastening on sample supports.

In order to ensure reliable holding of the sample 12 on the hydrophilic surface 57, a moist gas 59 is delivered through the tube 56. Since the gripping of the sample 12 with the aid of the patch pipette 54 takes place while still in the vacuum chamber 32 of FIG. 8, a moist film which ensures reliable holding of the sample 12 on the hydrophilic surface 57 is formed reproducibly by the moist gas 59.

Figure 14:
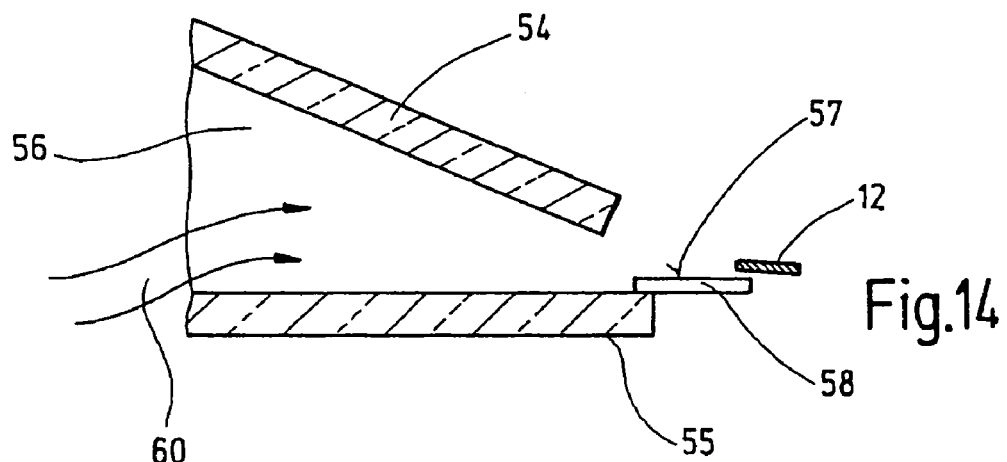
FIG. 14 shows a drawn glass capillary as in FIG. 13, but with the hydrophilic surface being designed as a nano-jaw protruding beyond the tip of the glass capillary.

In order to be able to remove the sample 12 from the hydrophilic surface 57 reproducibly and without mechanical stresses, a dry gas 60 is delivered through the tube 56, which is shown in FIG. 14. This dry gas 60 dries off the moisture film from the hydrophilic surface 57 such that the sample 12 is released from the hydrophilic surface 57, so that the sample can be deposited in a defined way.

Figure 15:
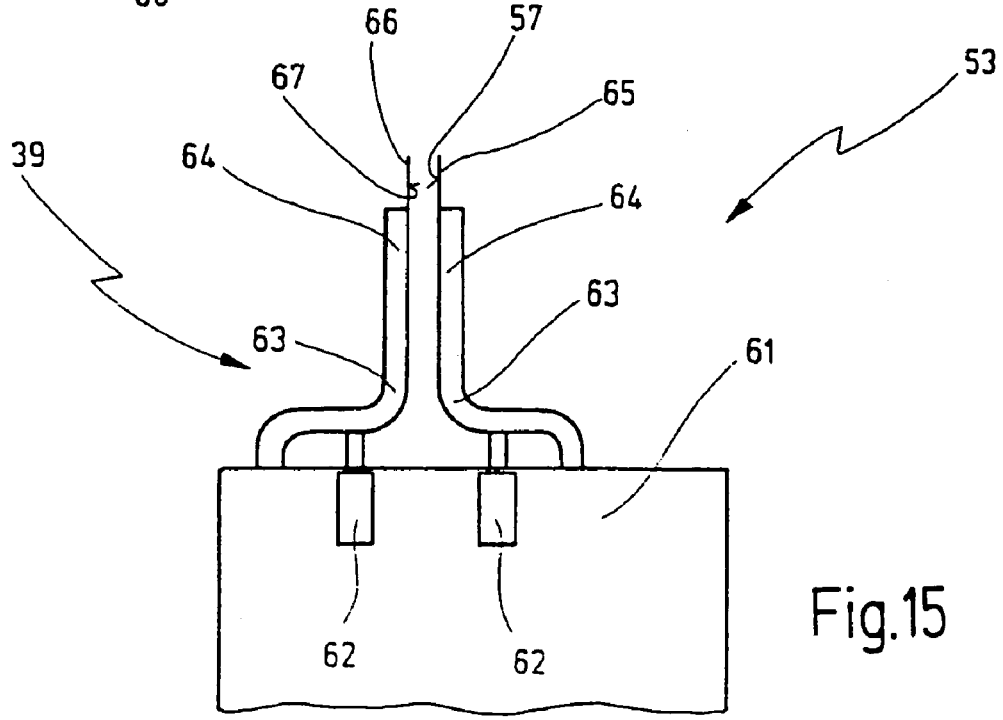
FIG. 15 shows a gripper which can be used in the scanning electron microscope of FIG. 8, having micromechanical pincer elements on which each a nano-jaw is fastened.

The gripper 39 known from FIG. 8, which is shown in a schematic plan view in FIG. 15, may also be used as the transport holder 53.

The gripper 39 is a micromechanical gripper which is formed on a circuit board 61 on which two electrostatic actuators 62 are provided, via which two micromechanical pincer elements 63 can be opened and closed in the manner of pincers. Such a micro-gripper is produced, for example, by the company Nascatec, Kassel, as mentioned at the outset.

The pincer elements 63 each have a nano-jaw 65 and 66 at their tip 64. Either the nano-jaws 65 and 66 may be produced by reprocessing the tips 64 using FIB, or the nano-jaws 65, 66 may be coupled to the tips 64 with the aid of EBID or IBID. The nano-jaw 65 is provided with the hydrophilic surface 57, while the nano-jaw 66 comprises a hydrophobic surface 67. In this way, it is possible first to collect the sample 12 with the aid of the hydrophilic surface 57 of the nano-jaw 65 and then to clamp the sample with the aid of the hydrophobic surface 67 of the nano-jaw 66. The sample 12 thus remains held reliably during transport inside the vacuum chamber.

In order to deposit the sample, the gripper 39 is then first opened, the sample remaining "bonded" reproducibly on the hydrophilic surface 57. By introducing a dry gas, the sample can then be deposited in a defined way.

Figure 16:
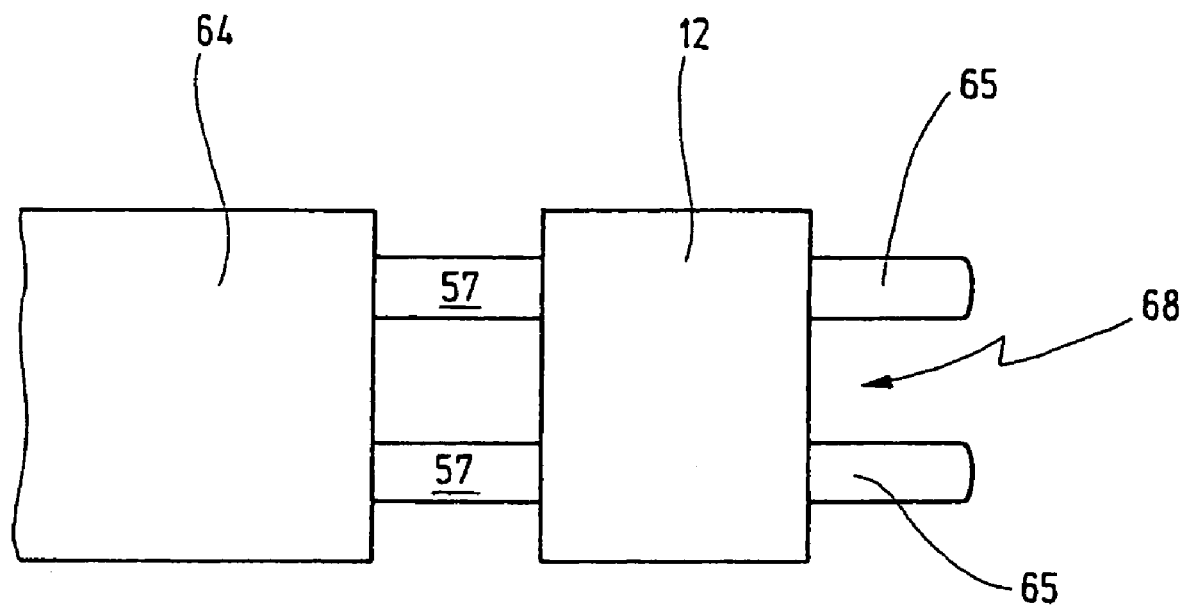
FIG. 16 shows a plan view of the tip of a pincer element of FIG. 15, the hydrophilic nano-jaw comprising a slot over which the sample comes to lie.
Figure 17:
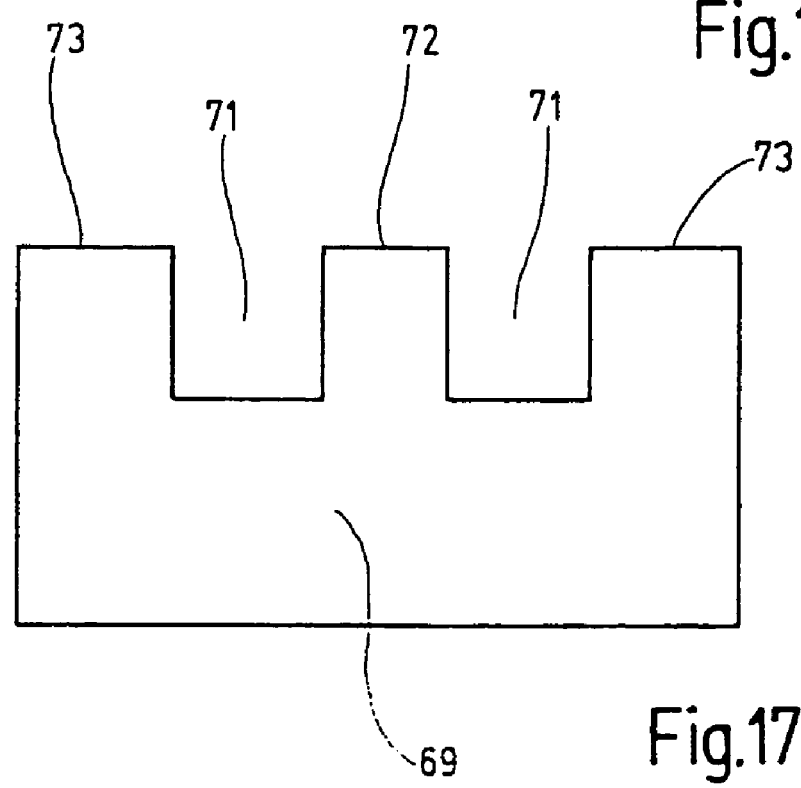
FIG. 17 shows a base which is adapted to the nano-jaw of FIG. 16, and on which the sample is placed.

FIG. 16 shows a plan view of the tips 64 of the pincer elements 63 of FIG. 15. Two nano-jaws 65 are fastened on the tips 64 so that they have a slot 68 between them, over which the sample 12 comes to lie. In this way, the sample 12 can be deposited in a defined way and without damage on a base 69 shown in FIG. 17, in which case the two nano-jaws 65 engage in two indentations 71 so that the sample 12 comes to lie on a segment 72 formed between the two indentations 71, and optionally on lateral segments 73. Defined placement of the sample 12 on the base 69 is thereby possible. If the release of the sample 12 from the hydrophilic surfaces 57 is furthermore assisted by a dry gas flushed around, there is likewise no risk of damage when depositing the sample 12.

Therefore, what is claimed, is:

1. A method for preparing a sample for electron microscopic examinations, in particular with a transmission electron microscope (TEM), comprising the steps:
    a) a substrate containing the sample to be prepared on a sample locus is provided in a vacuum chamber,
    b) a protective layer is applied onto a surface of the sample locus,
    c) the sample located under the protective layer is separated from the substrate by an ion beam, the protective layer acting as a mask, and
    d) in the vacuum chamber, the separated sample is removed from the substrate,
    wherein the sample is joined in step c) or d) to a TEM sample support which is moved by a manipulator, said TEM sample support comprising a holding end and a needle on which a thin tip is formed, the sample support being used for preparation and simultaneous mechanical fixing of the sample, whereby the holding end is selected from the group consisting of a TEM support grid, a metal angle segment disk, and a copper half-disk, whereby said needle is fastened to said holding end or formed integrally therewith.

2. The method of claim 1, wherein in step b), the protective layer is deposited on the surface with the aid of a focused particle beam.

3. The method of claim 2, wherein in step b), a focused particle beam, in particular an electron beam (EBID), ion beam or photon beam is used.

4. The method of claim 1, wherein in step b), the protective layer is applied onto the surface as a mechanical cover.

5. The method of claim 4, wherein in step b), a nanotube or fine nanowire is applied onto the surface as the mechanical cover.

6. The method of claim 1, wherein in step b), the protective layer is applied onto the surface by spraying or evaporation.

7. The method of claim 6, wherein in step b), the protective layer is sprayed onto the surface with the aid of a shadow mask.

8. The method of claim 1, wherein the protective layer comprises a material that is weakly etchable by ions.

9. The method of claim 1, wherein in step a), the substrate is placed in a scanning electron microscope (SEM) and a section of the substrate containing the sample locus is imaged using the SEM.

10. The method of claim 9, wherein in step c), the sample is first partially separated from the substrate, then the sample support is joined to the sample, and then the sample is fully separated from the substrate, the full separation being carried out by the ion beam or by breaking the sample out mechanically.

11. The method of claim 1, wherein in step c), the sample is separated from the substrate by a broad ion beam (SAIB).

12. The method of claim 11, wherein in step c), the sample is first partially separated from the substrate, then the sample support is joined to the sample, and then the sample is fully separated from the substrate, the full separation being carried out by the ion beam or by breaking the sample out mechanically.

13. The method of claim 1, wherein in step c), a low-energy ion beam is used.

14. The method of claim 13, wherein said low-energy ion-beam has an ion energy of less than 10 keV.

15. The method of claim 13, wherein said low-energy ion-beam has an ion energy of less than 5 keV.

16. The method of claim 1, wherein in step c), the sample is first partially separated from the substrate, then the sample support is joined to the sample, and then the sample is fully separated from the substrate, the full separation being carried out by the ion beam or by breaking the sample out mechanically.

17. The method of claim 1, wherein the sample support is gripped at its thicker holding end by the manipulator and, in step c) or d), fastened with its thin tip to the sample.

18. The method of claim 1, wherein in step c) or d), the sample support, preferably with its thin tip, is fastened to the sample by electron beam deposition or using a drop of adhesive.

19. The method of claim 18, wherein in step c) or d), the sample support is fastened with its thin tip to the sample by electron beam deposition or using a drop of adhesive.

20. The method of claim 1, wherein the holding end is designed as a circle segment or sector.

21. The method of claim 1, wherein in step d), the sample removed from the substrate is placed with the sample support in a TEM sample rod, to which the sample support is subsequently fastened.

22. The method of claim 1, wherein the sample has a thickness of from approximately 5 to approximately 200 nm and a length of approximately 1 to approximately 200 µm.

23. A TEM sample support for electron microscopic examinations in connection with a transmission electron microscope (TEM), said support having a holding end to be gripped by a manipulator and a needle connected to the holding end, said needle having a thin tip to be fastened to a sample for said electron microscopic examinations, said holding end being selected from the group consisting of a TEM support grid circle segment, a TEM support grid sector, and a metal angle segment disk.

24. The TEM sample support of claim 23, wherein the TEM support grid or the angle segment disk has a radius of from approximately 500 µm to approximately 2 mm and the needle has a length in the region of the radius of the TEM support grid, the needle having a diameter of from approximately 100 nm to approximately 10 µm in the region of its thin tip.

25. A method for preparing a sample for electron microscopic examinations, in particular with a transmission electron microscope (TEM), comprising the steps:
    a) a substrate containing the sample to be prepared on a sample locus is provided in a vacuum chamber,
    b) a protective layer is applied onto a surface of the sample locus, c) the sample located under the protective layer is separated from the substrate by an ion beam, the protective layer acting as a mask, and d) in the vacuum chamber, the separated sample is removed from the substrate, wherein in step c) or d), the sample is held by adhesion on a hydrophilic surface formed or fastened on a tip of a transport holder moved by a manipulator.

26. The method of claim 25, wherein in step c) or d), a moist gas is directed onto the hydrophilic surface before removal of the sample from the substrate.

27. The method of claim 26, wherein in step d), a dry gas is directed onto the hydrophilic surface after removal of the sample from the substrate.

28. The method of claim 25, wherein the hydrophilic surface has a slot, the sample being positioned on the hydrophilic surface so that it comes to lie over the slot, and in that, after removal from the substrate, the sample is placed on a base engaging in the slot and that the hydrophilic surface is then removed from the sample in the direction of the base.

29. The method of claim 25, wherein in step d), the sample is pressed against the hydrophilic surface by a hydrophobic surface of the transport holder.

30. The method of claim 29, wherein said transport holder comprises a gripper having two nano-jaws, one jaw comprising said hydrophilic surface and the other jaw comprising said hydrophobic surface.

31. The method of claim 25, wherein said transport holder is selected from the group consisting of a drawn glass capillary and a patch pipette, whereby said hydrophilic surface is formed on a tip of said transport holder.

32. A transport holder for gripping a sample for electron microscopic examinations, in particular with a transmission electron microscope, said transport holder comprising a gripper having two micromechanical pincer elements, each pincer element being provided with a nano-jaw, one jaw comprising a hydrophilic surface and the other jaw comprising a hydrophobic surface.

33. The gripper of claim 32, wherein each nano-jaw has a length of from approximately 100 nm to approximately 10 μm and a width of from approximately 100 nm to approximately 10 μm.

34. A transport holder for holding a sample for electron microscopic examinations, in particular with a transmission electron microscope (TEM), said holder comprising a drawn glass capillary having a hollow tube open at its tip and a hydrophilic surface fastened on said tip, and means for receiving said transport holder in a manipulator.

35. A TEM sample support for electron microscopic examinations in connection with a transmission electron microscope (TEM), said support having a holding end to be gripped by a manipulator and a needle connected to the holding end, said needle having a thin tip to be fastened to a sample for said electron microscopic examinations, said holding end comprising a TEM support grid.

* * * * *